United States Patent [19]
Malinouskas et al.

[11] Patent Number: 5,865,733
[45] Date of Patent: Feb. 2, 1999

[54] WIRELESS OPTICAL PATIENT MONITORING APPARATUS

[75] Inventors: Donald Malinouskas, Monroe; George Hojaiban, Meriden, both of Conn.

[73] Assignee: Spacelabs Medical, Inc., Redmond, Wash.

[21] Appl. No.: 808,559

[22] Filed: Feb. 28, 1997

[51] Int. Cl.[6] ................................................ A61B 5/02
[52] U.S. Cl. ................ 600/300; 600/453; 600/591; 128/903
[58] Field of Search .................. 128/661.07, 662.04, 128/698, 733, 738, 775, 903, 908; 600/300, 453, 591

[56] References Cited

U.S. PATENT DOCUMENTS

| | | | |
|---|---|---|---|
| 4,361,153 | 11/1982 | Slocum et al. | 128/903 X |
| 4,413,629 | 11/1983 | Durley, III | 128/662.04 X |
| 5,304,209 | 4/1994 | Adams et al. | 128/903 X |
| 5,373,852 | 12/1994 | Harrison et al. | 128/736 X |
| 5,387,259 | 2/1995 | Davidson | 128/908 X |
| 5,483,970 | 1/1996 | Rosenberg | 128/903 X |
| 5,511,553 | 4/1996 | Segalowitz . | |

FOREIGN PATENT DOCUMENTS

| | | |
|---|---|---|
| 0 367 251 A1 | 5/1990 | European Pat. Off. . |
| 3 609 913 A1 | 10/1987 | Germany . |

*Primary Examiner*—Francis J. Jaworski
*Attorney, Agent, or Firm*—Seed and Berry LLP

[57] ABSTRACT

A wireless patient monitoring apparatus uses an optical signal to transmit information from a transducer to a photodetector of an optical receiver. The photodetector converts the optical signal to an electrical signal which is then provided to monitoring and analysis instrumentation. Signals which are indicative of physiological functions are modulated onto a carrier, and the resulting modulated signal is provided, in turn, to the optical source, which may be a light-emitting diode (LED) which emits in the infrared band. A self-contained portable transducer assembly which is strapped or otherwise secured to the patient may house the transducer, modulator and optical source, and is adapted for underwater use. Optionally, the optical source can be positioned remote from the assembly. In a fetal monitor implementation, both wireless ultrasound and tocodynamometer transducers are provided.

32 Claims, 9 Drawing Sheets

WIRELESS OPTICAL PATIENT MONITORING APPARATUS

BACKGROUND OF THE INVENTION

The present invention relates to patient monitoring apparatus such as fetal monitoring apparatus, and more particularly to a novel wireless patient monitoring apparatus that uses optical signals such as those within the infrared band.

Apparatus for the real-time monitoring of physiological conditions in medical patients is well known. Examples of such apparatus include electrocardiogram recorders, heart rate monitors, electroencephalograph apparatus, maternal uterine activity monitors, and various other noninvasive medical instrumentation. Technology for monitoring such physiological functions includes ultrasound and tocodynamometer (TOCO) transducers. One type of instrumentation that benefits from the use of both ultrasound and tocodynamometer transducers is a fetal monitor, such as the Model IM77 Intrapartum Fetal Monitor manufactured by Advanced Medical Systems, Inc. of Hamden, Conn., U.S.A. This fetal monitor measures and records maternal and fetal activity during pregnancy through labor and delivery. Data on the fetal heart rate (FHR) and uterine activity (UA) is displayed on a front panel and simultaneously recorded on a trace (strip chart) recorder. FHR can be measured externally using Doppler ultrasound. Uterine activity can be measured externally using a TOCO transducer that incorporates, e.g., a strain gauge.

A disadvantage with prior patient monitoring systems, such as fetal monitors, is that the various transducers used to detect physiological functions required electrical cables in order to communicate the transducer signals to a console containing the user interface, analysis circuitry and output devices (e.g., strip chart recorder) used by medical professionals. Often, such cables become tangled, interfere with other medical procedures, and typically get in the way of the patient wearing them. Moreover, the need to be connected by cables limits the mobility of the patient and can cause discomfort. Additionally, wired transducers which are connected to a console that contains potentially dangerous electrical currents cannot be used in underwater deliveries or aqua therapy due to safety concerns. Water therapy is becoming increasingly common as it is believed to be beneficial to the laboring mother in alleviating some of the pain, and in speeding infant descent.

Past attempts to overcome the problems inherent with cabled transducers have focused on using telemetry (i.e., radio frequency signals) to provide wireless transducers. Although RF telemetry is advantageous in certain respects (such as a long range of operation which facilitates patient mobility), it also has various disadvantages in certain applications. For example, where different patients are being monitored in the same hospital, each monitor will have to operate at a different frequency to avoid conflict. Telemetry is also relatively costly to implement due to various transmitter and receiver requirements and the fact that government approval (e.g., by the Federal Communications Commission—FCC) is typically required. Telemetry fetal monitoring systems are also not well suited for aqua therapy.

Accordingly, it would be advantageous to provide a wireless patient monitoring system that avoids the disadvantages of cabled transducers. Such apparatus should be compact, compatible with fetal monitors, easy to use, and reliable.

The present invention provides a wireless patient monitoring system enjoying the aforementioned and other advantages.

SUMMARY OF THE INVENTION

In accordance with the present invention, wireless patient monitoring apparatus is provided, in which a transducer detects a physiological function. The transducer provides an output signal which is indicative of the physiological function. A modulator is provided for modulating a carrier by the transducer output signal. The modulated carrier is then provided to an optical source such as a light emitting diode (LED) which emits a corresponding optical signal in the infrared band. The optical signal is transmitted in a direction such that it can be received by a photodetector of a remote optical receiver. A monitoring circuit is coupled to receive the modulated optical signal from the optical receiver. The transducer is designed for placement adjacent to a region of a patient to be monitored.

In an illustrated embodiment, the transducer, modulator, and optical source are all situated in a common transducer housing. For example, the optical source may be secured to the top cover of the housing. Optionally, the optical source can be positioned remotely from the housing. For example, the optical source may be carried by a clip which is secured to the patient's clothing or body, where a wire couples the modulated carrier in the housing to the optical source.

A power supply is provided in the housing for powering the transducer, modulator, optical source, and associated circuitry situated in the housing. Optionally, a motion sensor situated in the housing detects movement of the housing. The power supply is responsive to the motion sensor for providing power when the housing is moved. A keep-alive circuit can be provided for actuating the power supply to continue to provide power when the physiological function is being detected. In this manner, battery power is conserved when the unit is not in use.

Preferably, the housing is waterproof. When the patient monitoring apparatus comprises a fetal monitor, a waterproof housing is particularly useful for underwater therapy. The optical receiver can be positioned above or otherwise within receiving range of the optical source.

In an embodiment where the patient monitoring apparatus is a fetal monitor, the transducer can comprise an ultrasound transducer adapted to be placed on a mother's abdomen to measure fetal heart rate. Alternatively, or in addition to the ultrasound transducer, a tocodynamometer transducer may be provided. The TOCO transducer is placed on the mother's abdomen for providing a TOCO output signal which is indicative of uterine activity. When both an ultrasound transducer and a TOCO transducer are used concurrently, they are generally positioned apart from one another, with the TOCO transducer slightly higher up on the abdomen than the ultrasound transducer. Separate housings may be used, although it is possible to use one common housing.

The TOCO transducer comprises a TOCO modulator which provides a signal to an optical source to provide the optical TOCO output signal. The photodetector of the optical receiver receives the modulated TOCO optical signal, converts it to an electrical signal, and provides the electrical signal to a monitoring circuit.

When both an ultrasound transducer and a TOCO transducer are used, each transducer may have an associated modulator, such as FM modulators, which operate at different frequencies. For example, the TOCO transducer output signal may be FM modulated on a 3,100 Hz carrier, and the ultrasound output signal may be FM modulated on an 8,000 Hz carrier. The modulated transducer signals may be provided to separate optical sources, or a common optical source may be used. Moreover, a common photodetector of the optical receiver may receive both the ultrasound and TOCO modulated optical signals, although it is also possible to provide photodetectors which are adapted to receive only a particular optical band.

Generally, it is convenient for the photodetector to be positioned above the optical source of the ultrasound and/or TOCO housings which are attached to the mother's abdomen, for example, by affixing the photodetector to a ceiling or overhead arm. Alternatively, when the optical source is remote from the housing, the photodetectors should be positioned accordingly. A number of photodetectors can be provided in different overhead positions to ensure clear reception of the transducer signal. Preferably the optical signal is provided as a wide-angle beam with sufficient power to ensure good reception.

A battery-operated power supply can be used to power the ultrasound and tocodynamometer transducers, together with their associated modulators and other circuitry. A first charging coil can be provided in each transducer housing for use in inductively charging the batteries. A receptacle is provided in a console portion of the patient monitoring apparatus for removably receiving the transducer housing. A second charging coil, located adjacent to the receptacle, inductively provides a charging current to the first charging coil when the transducer housing is placed in the receptacle. Means are provided for communicating a low battery signal to an external alarm via the optical signal. For example, a low battery signal can be modulated on the optical signal together with the transducer output information. When the monitoring circuit detects the low battery signal, it can actuate a signal to alert medical personnel to change the batteries in the transducer housing. Alternatively, a low battery condition can be signaled by slightly shifting the frequency of the carrier.

An optical receiver is provided for use with a wireless patient monitoring system. The optical receiver includes one or more photodetectors which are positioned to receive an optical signal which carries physiological information from a physiological function detector, such as the above-mentioned ultrasound and/or TOCO units. The photodetector converts the optical signal into a corresponding electrical signal which is, in turn, provided to a patient monitoring apparatus.

DETAILED DESCRIPTION OF THE INVENTION

The wireless optical patient monitoring system of the present invention enables physiological functions to be monitored without the inconvenience of having multiple connecting cables attached between the transducers placed on the patient and the bedside monitoring instrumentation.

Figure 1:
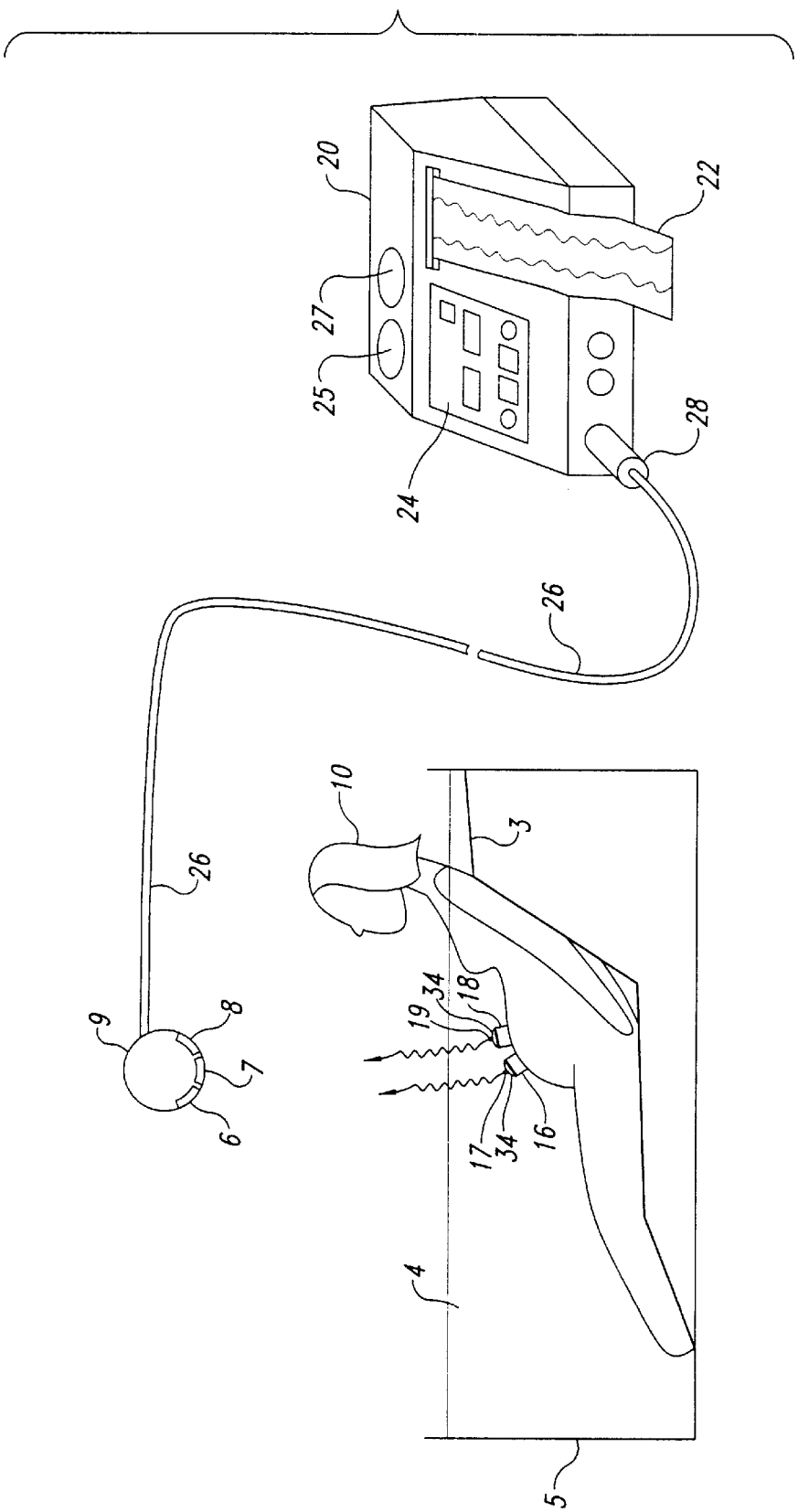
FIG. 1 is a diagram illustrating a wireless patient monitoring system in use in accordance with the present invention.

FIG. 1 illustrates an example implementation of the invention, in which wireless fetal heart rate and maternal uterine monitoring is provided. A patient 10 is monitored while lying on a surface 3 of a tub 5. Such tubs are commonly used in water therapy for the laboring mother. An ultrasound transducer assembly 16 is provided for monitoring fetal heart beat. A tocodynamometer transducer ("TOCO" or "TOCO transducer") assembly 18 is provided for monitoring maternal uterine activity.

Each of the transducer assemblies 16 and 18 is shown being submerged in water 4 of the tub 5. Additionally, each of the transducer assemblies 16 and 18 includes an optical source for providing an optical output signal which is indicative of the physiological function being monitored. Thus, in the case of the ultrasound transducer assembly 16, an optical source 17 provides an optical output signal which is indicative of fetal heart rate. The TOCO transducer assembly 18 includes a strain gauge or the like and an optical source 19 for providing an optical output signal which is indicative of uterine activity. The transducer assemblies 16, 18 may be affixed to the patient 10 via a strap, adhesive tape, or the like. When a strap is used, it is convenient for the optical sources (e.g., LEDs) 17, 19 to be disposed within knobs which protrude from the top cover 34 of the assemblies 16, 18 for engaging the strap. Alternatively, it is possible to provide a single assembly which incorporates the functions of the assemblies 16, 18, or to couple the assemblies 16, 18, so that one optical output signal is provided which includes both the ultrasound and TOCO information. Various known multiplexing techniques may be employed for this purpose. In another alternative embodiment, the optical sources 17 or 19 may be located remotely from the assemblies 16 or 18.

Figure 9:
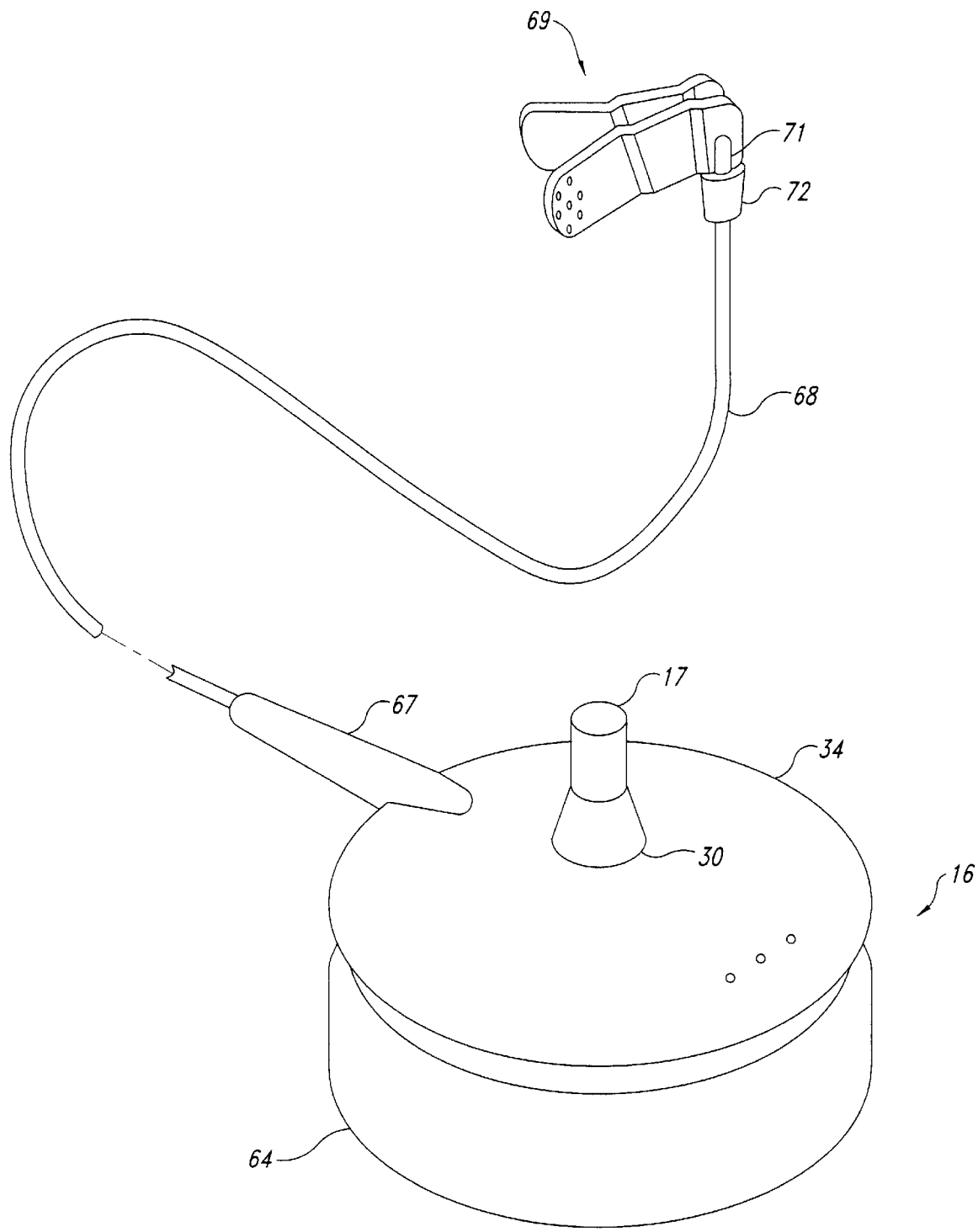
FIG. 9 is a diagram illustrating a wireless patient monitoring system with a remote optical source in accordance with the present invention.

FIG. 9 is a diagram illustrating a wireless patient monitoring system with a remote optical source in accordance with the present invention. Here, the optical source is adapted to be secured to the patient, for example, to clothing in the shoulder area, to the patient's ear lobe, or on a necklace, in order to increase the patient's mobility while still having the optical source emit an optical signal that can be received by the photodetector. The photodetector may be mounted on a wall or ceiling of the patient's room.

The transducer assembly 16 includes a top cover 34, optical source 17, knob 30, and base assembly 64, as discussed in further detail in connection with FIG. 2. An electrical connector 67 is mated with a port in the assembly 16 to carry the modulated transducer signal through a wire 68 to an optical source 71, which is held within a mounting 72. The optical source 71 and mounting 72 can be secured to the holder 69 using a variety of techniques which are known to those skilled in the art. The holder 69 can then be secured to the patient's clothing or body so that the patient will be free to move around while the monitoring process continues. The holder 69 may be a clip or other convenient mechanism such as, e.g., a hook and loop fastener, pin, arm band, or the like.

It will be understood that the remote optical source 71 may be provided by itself, or in addition to the optical source 17 which is on the top cover 34 of the assembly 16. For example, it is possible to have the remote optical source 71 permanently or releasably coupled to the assembly 16, in which case the optical source 17 is not required. Alternatively, a switch may be employed in a manner known to those skilled in the art to switch between the remote optical source 71 and the assembly-mounted optical source 17. Such a switch may be actuated by the insertion of the connector 67 into the assembly 16. It is further possible to have both optical sources 17 and 71 illuminated at the same time, although this may not yield the best results since the on-board battery power is limited.

It is also possible to couple the optical signal from the assembly-mounted optical source 17 to the remote optical source by converting the optical signal to an electrical signal, and then coupling the electrical signal to the remote optical source. A connector with a photodetector which fits over the optical source 17 could be used for this purpose. In a further option, the optical signal from the assembly-mounted optical source 17 could be coupled to a lens at the clip by using a light conducting member such as an optical fiber, although attenuation may be a concern. In this case, the lens itself is considered an optical source. Generally, the term "optical source" is used herein to encompass a point at which an optical signal originates as well as any intermediate point through which the optical signal propagates.

Referring again to FIG. 1, both of the transducer assemblies 16, 18 include modulators for modulating a carrier by the respective output signal produced by the transducer within the transducer assembly. Although relatively low frequency carriers are used in the illustrated embodiment, it should be understood that other frequencies may also be used successfully in accordance with the invention.

For example, the ultrasonic transducer incorporated in transducer assembly 16 can provide a modulator operating at 8,000 Hz, and the TOCO transducer can provide a modulator operating at 3,100 Hz. These frequencies are desirable since they are non-interfering (e.g, they do not have common harmonics). Of course, other frequencies can be used, and should preferably be non-interfering (non-mixing). In the illustrated embodiments, FM modulation is used. However, it should be appreciated that other well known types of modulation, such as amplitude modulation (AM) could alternatively be used.

The transducer assemblies 16, 18 include respective optical sources 17, 19, for providing corresponding optical output signals. In the embodiment illustrated in FIG. 1, the optical sources 17, 19 protrude from the assemblies 16, 18, respectively, and are positioned on top covers 34 of the assemblies. The optical sources may comprise, for example, light-emitting diodes (LEDs) which emit in the infrared radiation band. The optical spectrum is generally considered to have three bands, namely the ultraviolet band, which includes wavelengths of 10–390 nanometers (nm), the visible band, which includes wavelengths of 390–760 nm, and the infrared band, which includes wavelengths of 760 nm to 1 millimeter (mm).

Alternatively, when infrared transmission is used, the optical sources 17, 19 need not protrude from the transducer assemblies, but may be disposed behind the top covers 34 of the assemblies. In this case, the top cover is preferably black to allow optimal transmissivity of the infrared optical signal.

As explained in further detail below, the transducer assemblies 16, 18 are self-contained, battery-operated units that do not require any external connections.

An optical receiver 9 which comprises one or more photodetectors 6, 7, 8 is positioned over the transducer assemblies 16, 18 to receive the optical signals. It will be appreciated that the receiver 9 and/or photodetectors 6, 7, 8 may be configured in a number of different ways. For example, the receiver 9 may be affixed to a ceiling, an arm or other fixture which overhangs the tub 5, or even in a position which is displaced laterally from the tub, such as a nearby wall. Generally, any convenient location is suitable as long as the receiver 9 remains within range of the optical signals.

The optical sources 17, 19 of the transducer assemblies 16, 18, respectively, radiate optical signals which are received by one or more of the photodetectors 6, 7, 8. Additionally, while only one receiver 9 is shown in FIG. 1, it will be appreciated that additional receivers may be provided. The optimum positioning of the receiver or receivers will vary depending on the position of the light sources 17, 19 of the transducer assemblies 16, 18. In particular, it is desirable for the photodetectors 6, 7, 8 of the receiver 9 to be within the line-of-sight of the optical signals, and close enough that the strength of the received optical signal is adequate. Only one photodetector need be provided with the receiver in many instances.

Furthermore, it should be noted that the optical sources 17, 19 will generally be submerged in the water 4 of the tub 5 during the underwater birthing process. The optical signals will therefore be diffracted when they emerge from the surface of the water 4. In accordance with Snell's law, the emerging optical signals will tend to be diffracted away from the vertical. However, this is not problematic as long as the transducer assemblies 16, 18 remain relatively upright and a wide-angle beam is used for the optical signals. Alternatively, it is possible to provide additional photodetectors which are positioned laterally from the tub 5 to ensure that the optical signals are detected.

At the receiver 9, the received optical signals are converted to electrical signals in a known manner and provided via a cable 26 to a connector 28 of a receiver which is located in a bedside fetal monitoring console 20. The cable 26 may also carry an electric signal for powering the receiver 9.

Alternatively, virtually any other means of communication may be used to communicate the transducer electric signals from the receiver 9 to the console 20., including a wireless path.

Additionally, it is possible for the receiver 9 to be built into the console 20 so that the cable 26 is not needed. For example, the receiver 9 may be located on a side of the console and still receive the optical signals, particularly if the console is positioned within the line-of-sight of the optical sources. The console may further be provided with a raised structure which carries the receiver 9 and/or photodetectors 6, 7, 8. In some cases, the photodetectors may be able to detect the optical signals after they are reflected off a ceiling, for example. A suitable reflective material may be provided for this purpose.

Within the console 20, a receiver demodulates the transducer electric signals to recover the ultrasound audio and uterine activity information, which is, in turn, provided to a fetal monitor for conventional processing. The console 20 includes a control panel 24 having standard controls such as a digital display, audio volume controls, recorder controls, and the like. A strip chart recorder outputs strip documentation of patient data and monitored physiological functions on strip 22. Receptacles 25 and 27 are provided for charging batteries located in the transducer assemblies 16 and 18.

Figure 4:
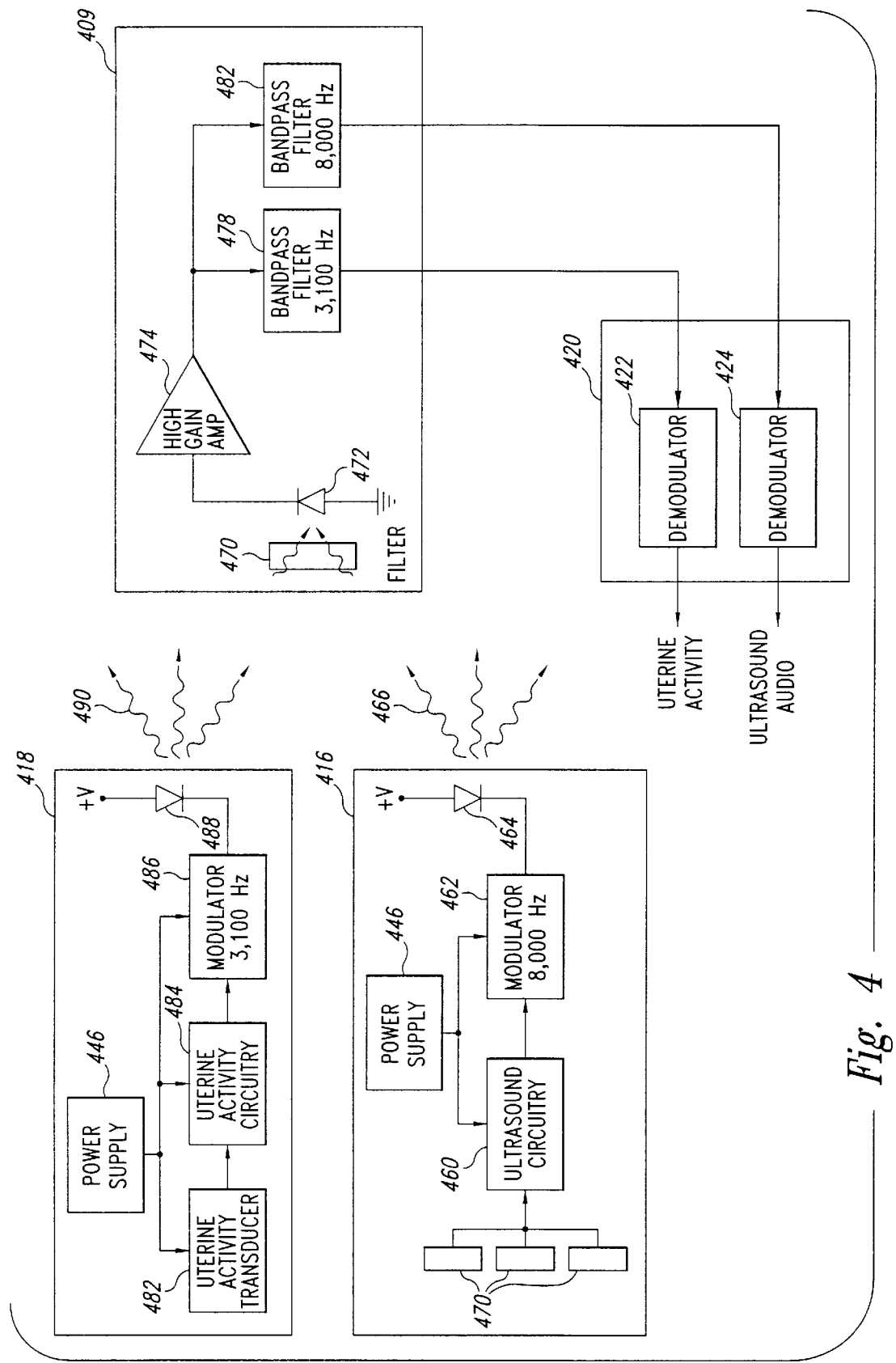
FIG. 4 is a block diagram of a wireless patient monitoring system in accordance with the present invention.

FIG. 4 is a block diagram of a wireless patient monitoring system in accordance with the present invention. An ultrasound processing function is shown at 416, while a TOCO processing function is shown at 418. The ultrasound function 416 includes a power supply 446 which powers ultrasound circuitry 460, an 8,000 Hz FM modulator 462, and a LED 464. Crystals 470 provide a signal to the ultrasound circuitry 460, where the signals are processed and subsequently modulated at the modulator 462. It should be noted that modulator 462 could alternatively comprise an AM modulator, which varies the intensity of the light output from LED 464. In a preferred embodiment, the LED 464 of the ultrasound processing function 416 emits infrared radiation 466, although visible light LEDs could alternatively be used. Further details of the ultrasound processing function 416 are discussed in connection with FIG. 5.

The TOCO processing function 418 includes a uterine activity transducer 482, uterine activity circuitry 484, a 3,100 Hz FM modulator 486 and a LED 488, all of which are powered by a power supply 446. The LED 488 emits, e.g., infrared radiation 490 in response to uterine activity. As with the ultrasound transducer, modulator 486 could alternatively comprise an AM modulator. Further details of the TOCO processing function 418 are discussed in connection with FIG. 7.

The infrared radiation 466, 490 from the ultrasound and TOCO processing functions 416, 418, respectively, travel to a receiver 409, and are filtered at a conventional filter 470 (such as black plastic), which serves to reject ambient light. A photodetector such as a photodiode 472 receives the infrared radiation and converts it into an electrical signal, which is then amplified at a high-gain amplifier 474.

The amplifier 474 may have a variable gain to accommodate different baseline levels of light transmission. Also, the amplifier preferably has a low end cut-off frequency which is substantially above 60 Hz in order to remove 60-cycle and other low-frequency interference signals. Furthermore, the low end cutoff frequency should be substantially below the lower of the two carrier frequencies (e.g., 3,100 Hz). Similarly, the high-end cut-off frequency should be substantially above the higher of the two carrier frequencies (e.g., 8,100 Hz).

The photodetector 472 is a photoelectric device which converts an optical signal into an electrical signal, and may include, for example, a photoconductive cell, photodiode, photoresistor, photoswitch, phototransistor, phototube, or photovoltaic cell. A photodiode, in particular, is a semiconductor diode in which the reverse current varies with illumination. The photodiode may be an alloy-junction photocell, or a grown-junction photocell.

The amplified electrical signal is then filtered at bandpass filters 478 and 482. The bandpass filter 478 is tuned to the carrier frequency of the TOCO modulator 486 (e.g., 3,100 Hz), while the bandpass filter 482 is tuned to the carrier frequency of the ultrasound modulator 462 (e.g., 8,000 Hz). The bandpass filters 478, 482 can also remove low-frequency interference. Each filter 478, 482 may comprise, for example, three filter stages for obtaining the desired separation between the high frequency carrier and low frequency carrier signals, while also providing sufficient bandwidth above the carrier frequency to pass the modulation signal which corresponds to the change in light intensity (AM modulation) or change in frequency (FM modulation) at the photodetector 472. Of course, any number of filter stages may be used. Further details of the receiver 409 are discussed in connection with FIG. 8.

The bandpass filters provide corresponding output signals to demodulators 422, 424 of the patient monitoring console 420. The demodulators 422, 424 separate the modulation signal from the carrier in a known manner to obtain a uterine activity signal and an ultrasound audio signal, respectively. Various demodulation techniques may be used, including rectification followed by low-pass filtering, synchronous detection, and the like.

Figure 2:
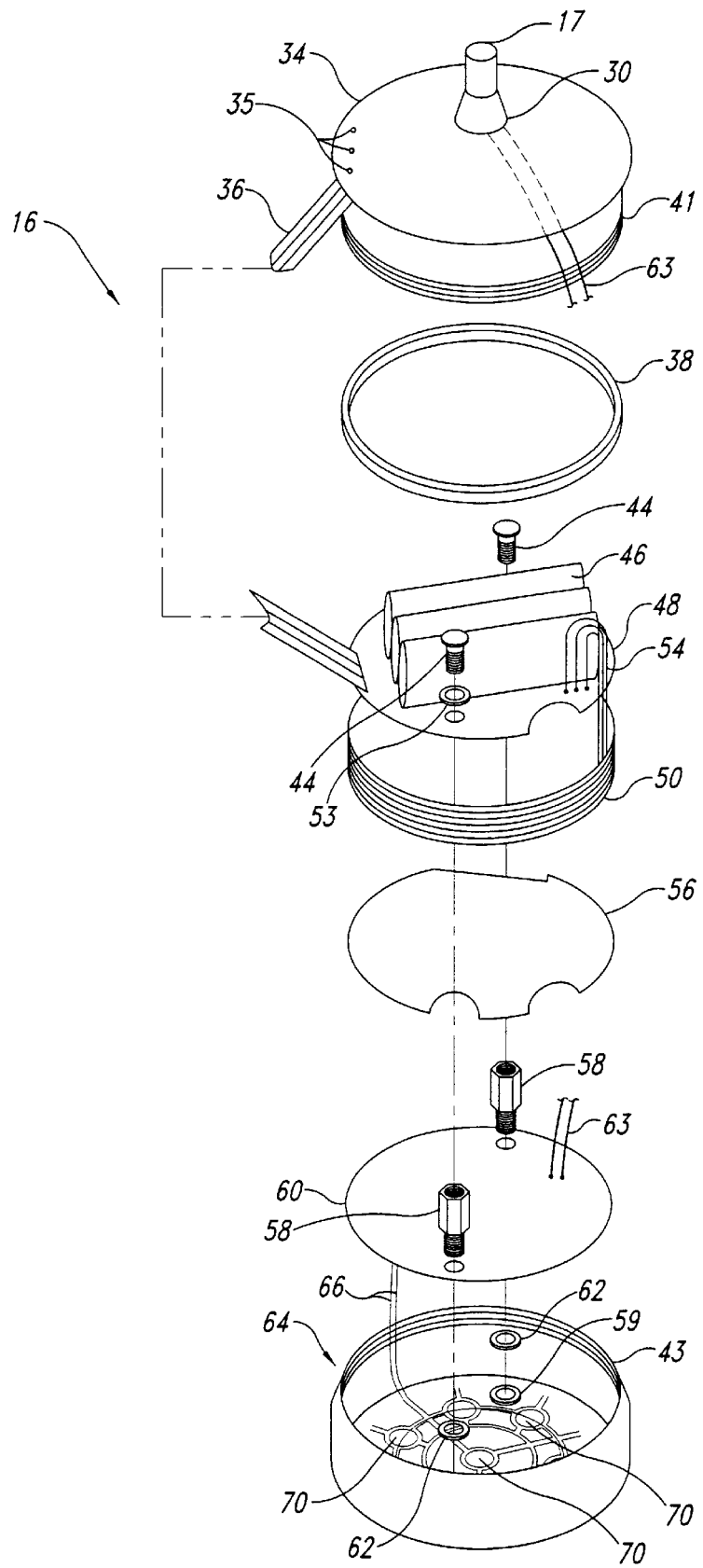
FIG. 2 is an exploded view of a wireless ultrasound transducer assembly.

FIG. 2 illustrates the ultrasound transducer assembly 16 in greater detail. A knob 30 is integral with an optical source such as a LED 17 and the top cover 34 of the assembly 16. The knob 30 can engage an opening in a strap that straps the transducer assembly onto the patient. The LED 17 and knob 30 are fastened on cover 34 in a watertight manner, such as via a room-temperature vulcanizing (RTV) silicone sealant. A threaded portion 41 of the top cover 34 engages a threaded portion 43 of a base assembly 64 to secure the assembly 16. A plurality of light emitting diodes (LEDs) 35 are provided in the top cover 34 for indicating the condition of rechargeable batteries 46 (e.g., nickel cadmium, or NiCad batteries) within the assembly. The LEDs 35 emit in the visible band. Wires 36 couple the LEDs 35 to a power supply printed circuit board 48 ("battery board"). An "O" ring 38 seals the top cover 34 against base assembly 64, so that the unit 16 is watertight when assembled.

The threaded connectors 44 screw into threaded connectors 58, which in turn are screwed into threaded receptacles 59 (only one shown) of base 64. Insulating washers 53 and 62 are provided as shown.

A coil 50 which is provided within the transducer assembly is a battery charging coil, which receives charging current inductively from either charging receptacle 25 or 27 of console 20 when the transducer assembly is inserted into the receptacle (FIG. 1). This coil can be constructed, for example, from 36 turns of 30 gauge solid copper wire, with a coil diameter of about 2.5 inches. The coil has a center tap which is grounded. A laminate Mylar/copper shield 56 is provided between the battery board 48 and an ultrasound transducer board 60, which contains circuitry for processing and modulating the ultrasound signals which are indicative of fetal heart rate. It should be understood that transducer board 60 is a printed circuit board containing various electronic components which are not specifically shown in the drawing. A pair of wires 63 are coupled to carry the modulated transducer signal from a modulator on the transducer board 60 to the LED 17.

In the embodiment illustrated in FIG. 2, seven ultrasonic transducer crystals 70 are mounted to the bottom of base 64. These crystals are coupled to the ultrasound transducer board 60 via wires 66.

Figure 3:
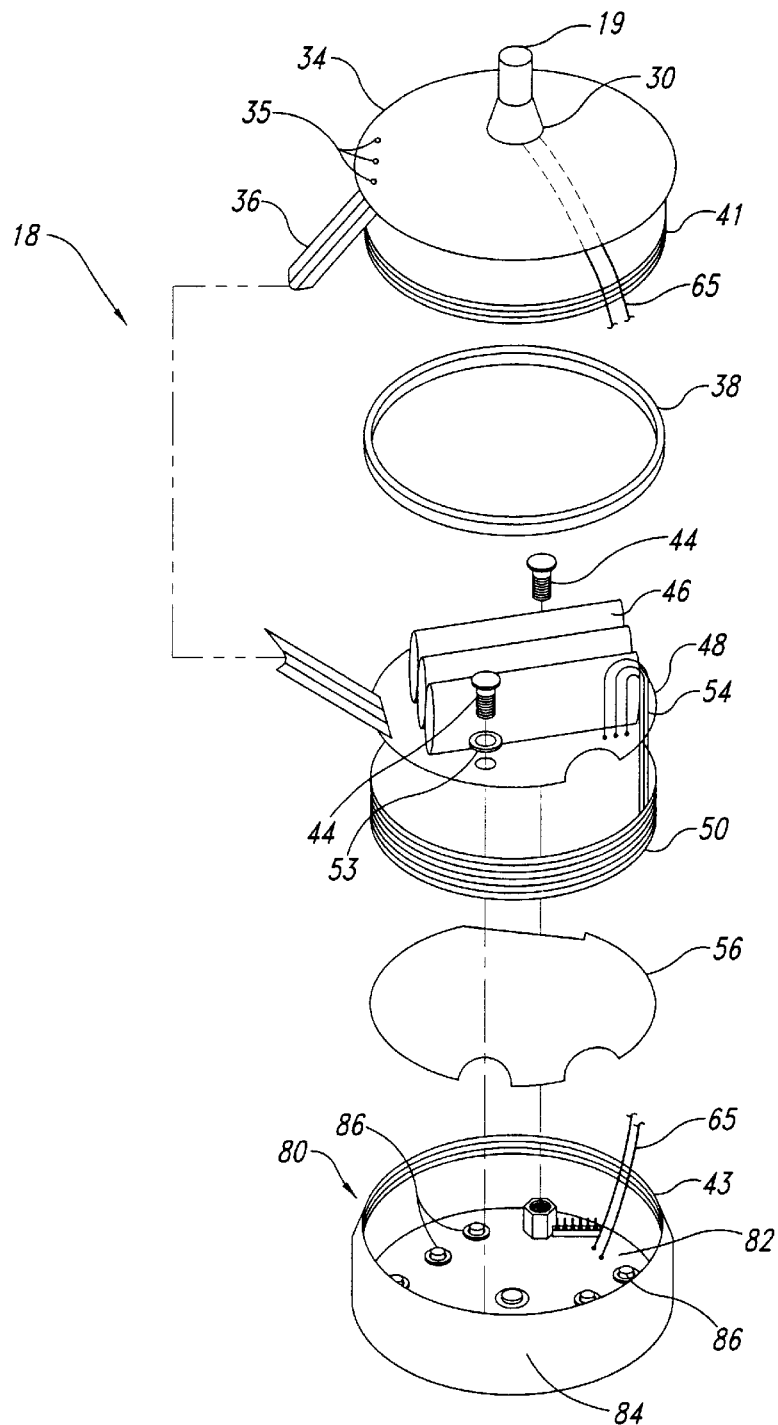
FIG. 3 is an exploded view of a wireless tocodynamometer transducer assembly.

FIG. 3 illustrates the TOCO transducer assembly 18 in greater detail. Parts which are identical with those of the ultrasound transducer bear the same reference numbers as in FIG. 2. The TOCO transducer differs from the ultrasound transducer in that instead of providing ultrasound printed circuit board 60, a TOCO transducer board 82 is provided. This PC board contains the circuitry required to process signals from a strain gauge 84 contained in the TOCO transducer base 80. The strain gauge is mounted to the TOCO transducer board 82 via fasteners 86, which can comprise small nuts and bolts. Wired TOCO transducers are well known in the art, and the assembly of the strain gauge within base 80 is conventional. A pair of wires 65 carry the modulated transducer signal from a modulator on the TOCO transducer board 82 to the LED 19, which is mounted in a watertight manner (e.g, using a sealant such as RTV silicone) in knob 30.

In FIGS. 2 and 3, the optical source (e.g., LED) 17 or 19 was shown protruding from the knob 30. Alternatively, it is possible for the LED 17 or 19 to be disposed beneath the top cover 34. In particular, when the LED emits in the infrared band, the transmissivity through the top cover 34 will be very high when the top cover 34 is manufactured from black plastic which passes radiation in the infrared spectrum. Other alternatives are possible, for example, the use of more than one transmitting LED on the top cover 34, the use of a lens for directing the radiation, or the use of LEDs on surfaces other than the top cover.

Figure 5:
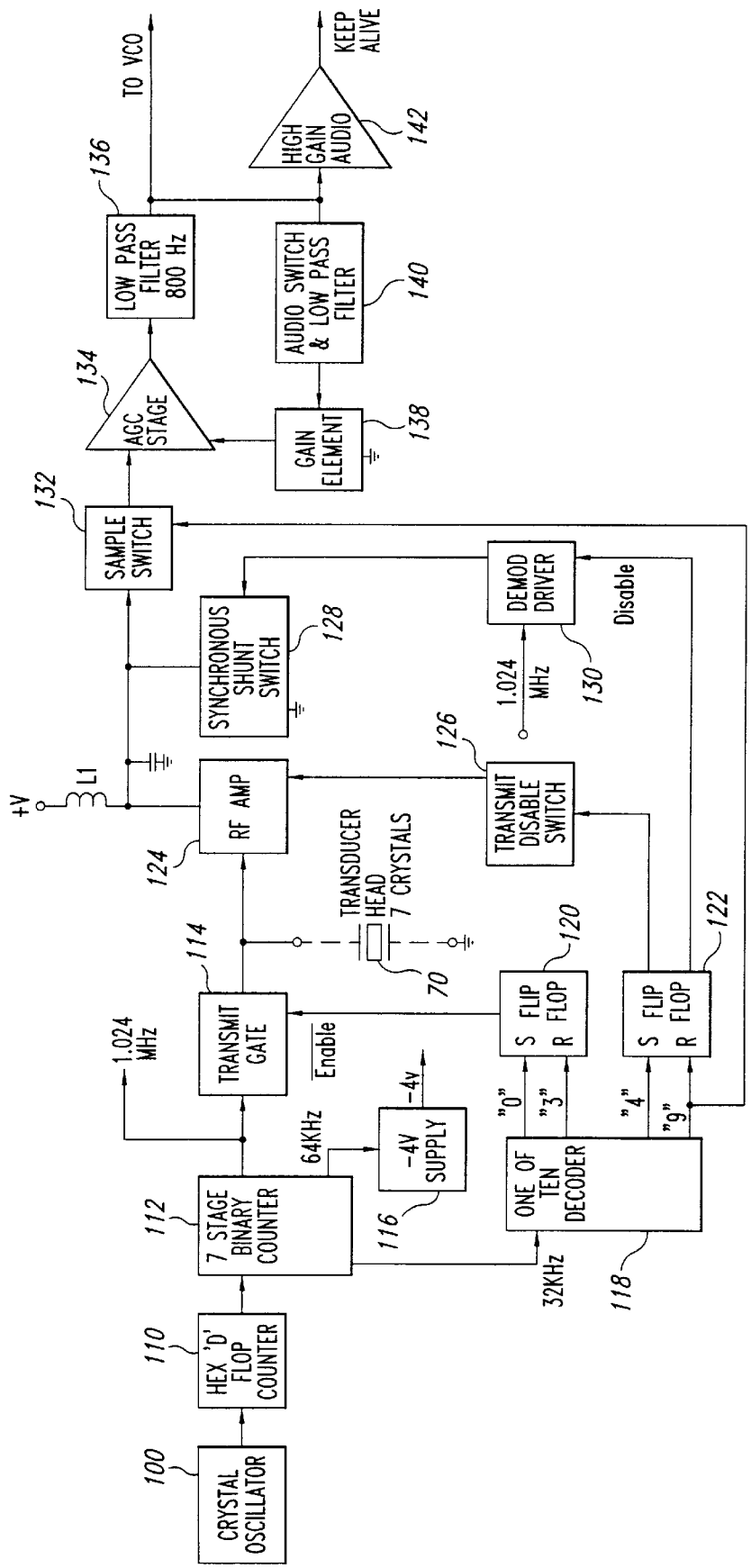
FIG. 5 is a block diagram illustrating circuitry incorporated into the ultrasound transducer of FIG. 2.

FIG. 5 is a block diagram of the ultrasound printed circuit board 60 illustrated in FIG. 2. The ultrasound transducer assembly contains a pulse Doppler transmitter and receiver. Such components are well known in the art. A crystal oscillator 100 (operating, e.g, at 6.144 MHz) feeds a HEX "D" flop counter 110, which divides the oscillator output by three to provide a 2.048 MHz output. A seven-stage binary counter 112 divides by two, to provide a 1.024 MHz output for driving the ultrasonic transducer crystals 70, through a transmit gate 114.

Counter 112 also supplies a 64 kHz output to a −4 volt supply 116 that is used to power various components on the ultrasound board. A 32 kHz output is provided from counter 112 to a one-of-ten decoder 118, which together with flip flops 120 and 122 and transmit disable switch 126 provide a desired pulse width for successive ultrasonic pulses and the waiting period therebetween. The 1.024 MHz output is directed from the transducer crystals to the fetal heart, and returns with a Doppler shift, such that the fetal heart sounds are detected over a range of about 50–300 Hz. An RF amplifier transistor 124 is used to amplify the output from the transducer crystals, in a conventional manner. A demodulator driver 130, which receives the 1.024 MHz signal, together with a synchronous shunt switch 128 are used to subtract out the 1.024 MHz input frequency from the Doppler shifted signal to provide the fetal heartbeat output in the 50–300 Hz range. A sample switch 132 avoids the need for complicated filtering, by taking short samples of the heart rate sounds at a high rate.

Figure 6:
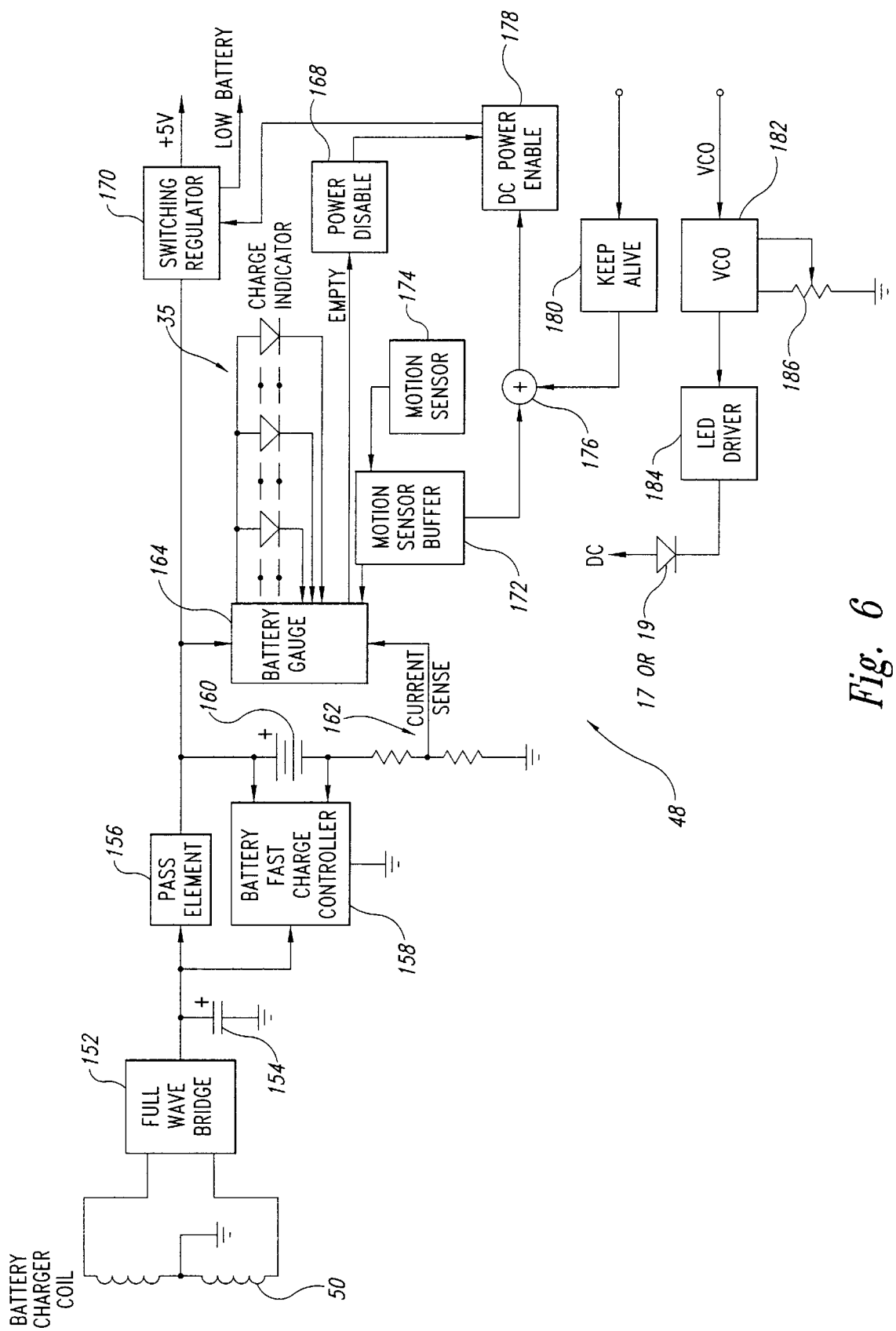
FIG. 6 is a block diagram illustrating power supply and oscillator circuitry found in the ultrasound transducer of FIG. 2 as well as the TOCO transducer of FIG. 3.

The samples output from switch 132 are input to an automatic gain control (AGC) loop containing an AGC stage 134, low pass filter 136, audio switch and low pass filter 140 and gain element 138. The AGC loop normalizes the amplitude of the audio before it is passed to the voltage controlled oscillator (VCO) 182 that drives the LED driver 184 (FIG. 6). In this manner, the VCO can transmit a strong signal without overdriving the output. A high gain audio amplifier 142 is provided for use with a keep-alive circuit described below in connection with FIG. 6.

FIG. 6 is a block diagram illustrating power supply and oscillator circuitry found in the ultrasound transducer of FIG. 2 as well as the TOCO transducer of FIG. 3. As indicated, the audio output from low pass filter 136 of the ultrasound board (FIG. 5) is input to a VCO 182. The audio signal is used to frequency modulate a subcarrier produced by VCO 182, and the subcarrier is applied to the LED 17 or 19 via an LED driver 184. As indicated above, the LED 17 or 19 may be mounted inside the knob 30 of the top cover 34 of the ultrasound transducer housing. The LED driver 184 can simply comprise a transistor which outputs an FM modulated sine wave. Variable resistor 186 is provided in order to adjust the frequency of VCO 182. For the ultrasound transducer, the nominal output frequency of VCO 182 is, e.g., 8,000 Hz and for the TOCO transducer, 3,100 Hz. Other frequencies can, of course, be used as long as they are chosen such that they do not substantially interfere with each other. The battery board 48 of FIG. 6 includes a battery charging circuit, a battery gauge, a motion sensor circuit for turning on power to the transducer assembly, and a keep-alive circuit for maintaining power when signals are being received. Essentially the same battery board can be used with the ultrasound transducer and the TOCO transducer.

To facilitate ease of use and provide a waterproof transducer case, battery power may be turned on via a motion sensing device. A motion sensor 174, which can comprise any type of switch that is activated by motion, provides an input to a motion sensor buffer 172. Examples of such switches include mercury switches and spring loaded mechanical switches that close a contact in response to any small motion. Upon a transition of the motion sensor contacts, an output signal generated by motion sensor buffer 172 is applied to an OR gate 176, the output of which activates a DC power enable circuit 178. In response, switching regulator 170 outputs power from battery pack 160.

After the transducer is placed onto a patient, a keep-alive circuit 180 senses the fetal heartbeat (ultrasound transducer) or uterine activity (TOCO transducer) and keeps the power on. The output of the keep-alive circuit is input to OR gate 176 to actuate DC power enable 178, which in turn actuates switching regulator 170 to output the battery power. The power remains on for a number of minutes after the transducer 16, 18 assembly is removed from the patient, by virtue of a timer in DC power enable circuit 178.

Each transducer assembly is powered by an internal rechargeable battery pack 160. Recharging is accomplished by placing the entire transducer into a receptacle 25 or 27 provided on the fetal monitor console 20 (FIG. 1). The charging station contains a coil for inductively charging the battery pack via battery charger coil 50. The current received from the charging station is passed through a full wave bridge rectifier 152 and filtered by capacitor 154. A pass element 156, which can comprise a simple transistor, passes the charging current on to the rechargeable battery pack 160. A fast charge battery controller 158, which is an off-the-shelf integrated circuit, terminates the charge current by either detecting full battery capacity or detecting that a maximum allowable charge time has elapsed. Once the battery is fully charged, a trickle charge is maintained to keep the battery at full capacity.

Battery current is sensed via a voltage divider 162 for input to a battery monitoring circuit ("battery gauge") 164. This integrated circuit keeps track of battery usage and charge currents. Compensation is made for diminished battery capacity due to age and self-discharge. Each time a complete charge/discharge cycle is performed, the programmed full capacity is updated.

Three LED indicators 35 show the approximate remaining battery charge. The LED indicators are illuminated for a brief time period after each detected motion, at the end of battery life, and when the transducer is placed into the charging station. When the battery is near the end of its useful charge, at least one of the LED indicators will flash and a signal may be transmitted to the fetal monitor console to notify the operator.

When the battery is discharged, a power disable circuit 168 responsive to the battery gauge actuates the DC power enable circuit 178 to turn off the switching regulator 170, thereby terminating the supply of power to the rest of the transducer circuitry. When the battery is low, the switching regulator outputs a "glow battery" signal which, in the case of the ultrasound transducer, can be used to slightly shift the VCO frequency via the variable frequency adjusting resistance 186. Upon detecting a shifted ultrasound carrier, the receiver in the fetal monitor console will actuate a suitable low battery indicator.

Figure 7:
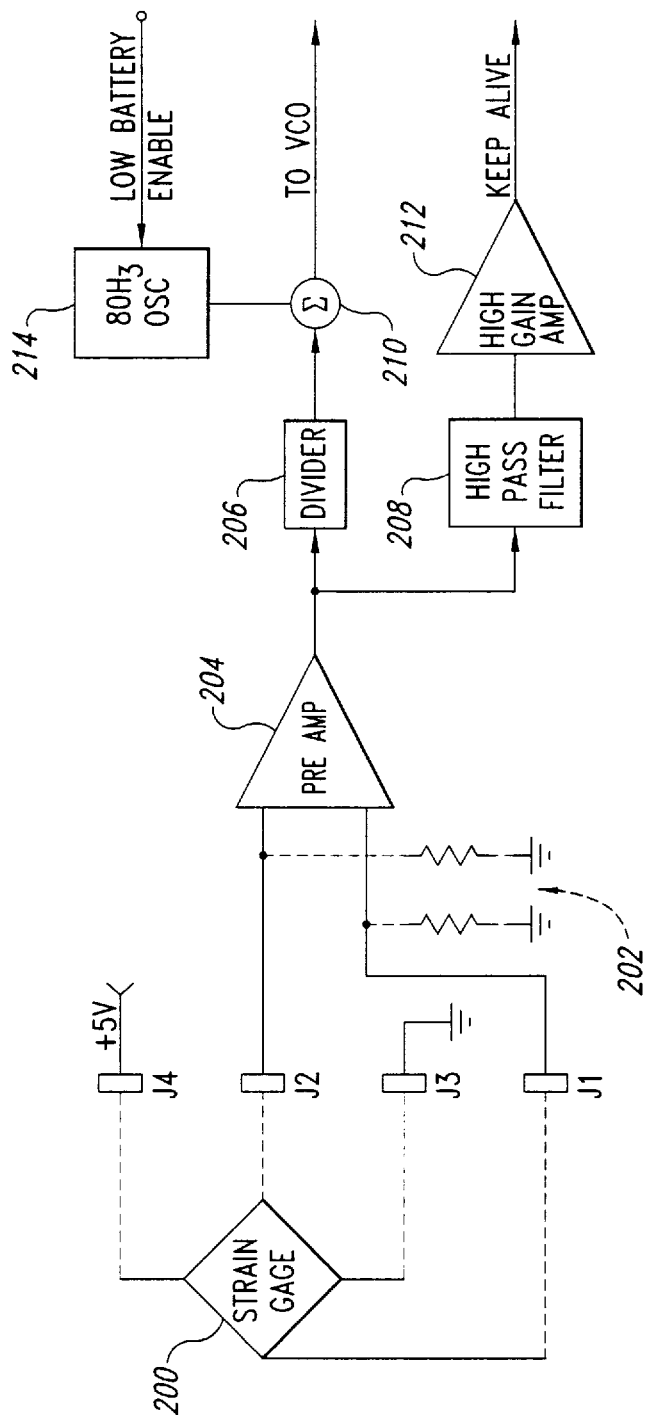
FIG. 7 is a block diagram of TOCO transducer circuitry found in the transducer of FIG. 3.

In the case of the TOCO transducer, the low battery signal from switching regular 170 is input to actuate an oscillator 214 as illustrated in FIG. 7. The oscillator output (e.g., 80 Hz) is summed with the output carrier which carries the TOCO transducer signal for detection by the receiver circuitry in the fetal monitor console.

FIG. 7 illustrates the circuitry contained on the TOCO transducer printed circuit board 82 of FIG. 3. A strain gauge 200 detects uterine activity and produces an output signal that is amplified in preamplifier 204. Optional offset adjusting resistors 202 are provided to balance the strain gauge outputs.

The amplified output from the strain gauge is scaled in a divider 206, and summed with the output of oscillator 214 (when present). The resultant signal is output to the VCO 182 of a corresponding battery board 48 illustrated in FIGS. 3 and 6. As indicated above in connection with the ultrasound transducer, the strain gauge output of the TOCO transducer will FM modulate the VCO on the battery board of the TOCO transducer assembly, for output to a LED driver 184 and LED 17.

The output of preamplifier 204 (FIG. 7) is also passed through a high pass filter 208 and a high gain amplifier 212 to provide a keep-alive signal that is input to the corresponding keep-alive circuit 180 on the TOCO transducer battery board. In this manner, once power to the TOCO transducer assembly is provided, it will remain as long as uterine activity is detected by the strain gauge, and for some predetermined time thereafter.

Figure 8:
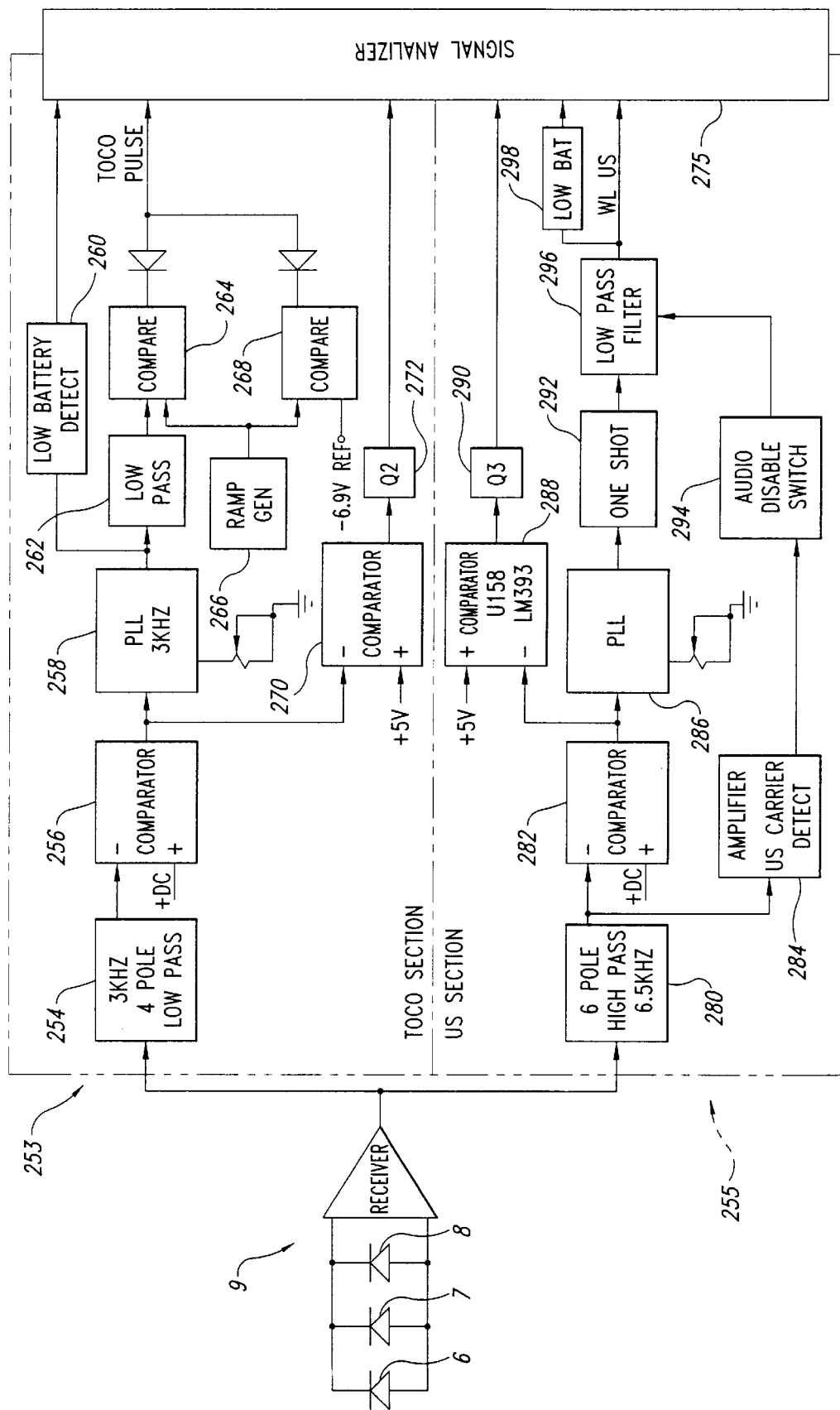
FIG. 8 is a block diagram illustrating a receiver for signals output from the ultrasound transducer of FIG. 2 and the TOCO transducer of FIG. 3.

FIG. 8 illustrates the receiver circuitry for processing the ultrasound and TOCO signals in the fetal monitor console 20. The optical signals from the LEDs 17, 19 of the transducer assemblies 16, 18, respectively, are received by photodetectors such as photodiodes 6, 7, and 8 of the receiver, shown generally at 9. See also FIG. 1. The received optical signal is converted to an electrical signal by the diodes 6, 7, 8 and may undergo additional processing by the receiver 9. Preferably, the TOCO and ultrasound carrier frequencies will be chosen to be noninterfering with each other or with other signals such as the pulse Doppler repetition frequency. It has been found that an ultrasound carrier frequency of 8,000 Hz and TOCO transducer carrier frequency of 3,100 Hz is satisfactory.

The output of the receiver 9 is input to a TOCO transducer processing circuit generally designated 253 and to ultrasound transducer processing circuitry generally designated 255. In the TOCO transducer section, the signal is received by a low pass filter 254 which passes the 3,100 Hz TOCO carrier to a comparator 256. The comparator compares the TOCO carrier to a DC level and outputs a square wave to a phase-lock-loop (PLL) circuit 258 which locks onto the input frequency. The output of the PLL is a representation of TOCO pressure. This signal is low pass filtered by filter 262 and converted to a digital signal by comparators 264 and 268 which also receive an input from ramp generator 266. As indicated in FIG. 8, comparator 264 compares the TOCO signal to the ramp generator output. Comparator 268 compares the ramp generator output to a reference voltage. The combined output of the comparators is a pulse width modulated signal representative of uterine activity, which is input to a conventional microprocessor controlled signal analyzer 275 in the fetal monitor console.

A comparator 270 is provided in the TOCO section of the receiver for detecting the presence of a wireless TOCO signal. If no wireless signal is present (i.e., no modulated TOCO carrier is detected), a transistor 272 will output a signal to signal analyzer 275 in order to switch the fetal monitor to a cable mode of operation. In the cable mode, the fetal monitor can use conventional wired transducer assemblies.

The ultrasound section of the receiver includes a high pass filter 280 that recovers the ultrasound transducer carrier from the signal output by the receiver 9. After processing by a comparator 282 and phase-lock-loop 286, the signal is demodulated using a monostable multivibrator (one-shot) 292 and low pass filter 296. The demodulated audio is then provided to the conventional signal analyzer 275.

An amplifier 284 detects the level of the ultrasound carrier. If the level is too weak, amplifier 284 actuates an audio disable switch 284 to mute the audio via low pass filter 296. A comparator 288 and transistor 290, analogous to comparator 270 and transistor 272 of the TOCO receiver circuitry, switch the fetal monitor to the cable mode of operation when no wireless ultrasound signal is present.

Both the TOCO section 253 and ultrasound section 255 are provided with respective low battery detection circuits 260, 298. The TOCO section low battery detection circuit 260 detects the 80 Hz signal added to the TOCO transducer output via an oscillator 214, discussed above in connection with FIG. 7. The ultrasound low battery detector 298 detects a frequency shift introduced via the VCO 182 in the ultrasound transducer assembly when the battery power is low, as discussed above in connection with FIG. 6. The detection of a low battery signal in either the TOCO transducer or the ultrasound transducer will result in a notification signal being generated in signal analyzer 275.

It should now be appreciated that the present invention provides a wireless patient monitoring apparatus in which an optical signal such as an infrared signal from a LED is used to communicate signals from self-contained, portable transducer assemblies to a patient monitoring apparatus. The optical signal is emitted from one or more LEDs which are located on the top cover of the transducer assembly, or remotely, and received by photodetectors of a receiver which may be positioned above the patient. The receiver can then send the signal to the patient monitoring apparatus via conventional wiring. Alternatively, the receiving photodetector may be mounted directly on the patient monitoring console.

The use of optical signals avoids the drawbacks of prior art radio frequency telemetry systems, such as interference with other instrumentation. Additionally, the disadvantages of wired systems are avoided, including inconvenience and interference with other equipment or personnel.

Moreover, the invention is particularly adapted for use in underwater birthing, where cables cannot be used due to the possibility of shock. Advantageously, no modification to the birthing tub is required.

Although the invention has been described in connection with a preferred embodiment, it should be appreciated that various adaptations and modifications may be made thereto without departing from the spirit and scope of the invention as set forth in the claims.

We claim:

1. An optical patient monitoring apparatus, comprising:
   a transducer for detecting a physiological function, said transducer being designed for placement on a patient to be monitored, and said transducer providing an output signal indicative of said physiological function;
   a modulator for modulating a carrier by said output signal;

a waterproof optical source associated with said modulator for emitting an optical signal which corresponds to said modulated carrier;

a photodetector for receiving said optical signal, said photodetector being adapted to receive said optical signal after said optical signal passes through a water-air boundary; and a monitoring circuit coupled to receive the modulated carrier from said photodetector.

2. An apparatus in accordance with claim 1, wherein:
said optical source is a light-emitting diode.

3. An apparatus in accordance with claim 1, wherein:
said optical source emits in an infrared band.

4. An apparatus in accordance with claim 1, further comprising:
an optical filter associated with said photodetector for filtering out interfering radiation.

5. An apparatus in accordance with claim 1, wherein:
said transducer and said optical source are adapted for use underwater.

6. An apparatus in accordance with claim 1, wherein:
said photodetector is adapted to be positioned above the patient to receive said optical signal.

7. An apparatus in accordance with claim 1, wherein:
said transducer, modulator and optical source are all situated in a common transducer housing.

8. An apparatus in accordance with claim 7, further comprising:
a power supply in said housing for powering said transducer, said modulator, and associated circuitry situated in the housing; and
a motion sensor situated in said housing for detecting movement of the housing;
wherein said power supply is responsive to said motion sensor for providing power when the housing is moved.

9. An apparatus in accordance with claim 8, further comprising:
a keep-alive circuit for actuating said power supply to continue to provide power when said physiological function is being detected.

10. An apparatus in accordance with claim 1, wherein:
said transducer and modulator are situated in a common transducer housing;
said optical source is adapted to be positioned remotely from said housing; and
means are provided for coupling said transducer housing and said optical source.

11. An apparatus in accordance with claim 1, wherein:
said transducer comprises a tocodynamometer (TOCO) transducer adapted to be placed on a mother's abdomen and said physiological function comprises uterine activity.

12. An apparatus in accordance with claim 1, wherein:
said transducer comprises an ultrasound transducer adapted to be placed on a mother's abdomen and said physiological function comprises fetal heart rate.

13. An apparatus in accordance with claim 1, further comprising:
a tocodynamometer (TOCO) transducer adapted to be placed on said abdomen for providing a TOCO output signal indicative of uterine activity, said TOCO transducer comprising a TOCO modulator for modulating a TOCO carrier by said TOCO output signal;
an optical source associated with said TOCO modulator for emitting a TOCO optical signal which corresponds to said TOCO modulated carrier;

a TOCO photodetector for receiving said TOCO optical signal; and
a monitoring circuit coupled to receive the TOCO modulated carrier from said TOCO photodetector.

14. An apparatus in accordance with claim 13, wherein:
the output signals from said ultrasound and tocodynamometer transducers are modulated on separate non-interfering subcarriers.

15. An apparatus in accordance with claim 1, wherein:
said transducer, modulator and optical source are all situated in a common transducer housing, said apparatus further comprising:
a battery-operated power supply in said housing for powering said transducer, said modulator, and associated circuitry situated in the housing; and
a first charging coil in said housing for use in inductively charging said batteries.

16. An apparatus in accordance with claim 15, further comprising:
a console containing said monitoring circuit;
a receptacle in said console for removably receiving said transducer housing; and
a second charging coil, located adjacent to said receptacle, for inductively providing a charging current to the first charging coil when the transducer housing is placed in said receptacle.

17. An apparatus in accordance with claim 15, further comprising:
means for communicating a low battery signal to an external indicator via said optical source and said photodetector when said battery-operated power supply is in a low charge state.

18. A receiver for use with an optical patient monitoring system, said system including a transducer which is designed for placement on a patient to be monitored, said receiver comprising;
a photodetector for receiving an optical signal which corresponds to a modulated signal carrying physiological information from said transducer, said photodetector being adapted to receive the optical signal after the optical signal passes through a water-air boundary, said modulated signal being transmitted from an optical source which is associated with said transducer; and
circuitry coupled to said photodetector for providing said modulated signal to a monitoring circuit of said patient monitoring apparatus.

19. A receiver in accordance with claim 18, further comprising:
an optical filter associated with said photodetector for filtering out interfering radiation.

20. A receiver in accordance with claim 18, wherein:
said photodetector is adapted to be positioned above the patient to receive said optical signal.

21. An optical source holder for use with a patient monitoring system, said system including a housing which provides a modulated signal carrying physiological information from a patient, wherein:
coupling means are provided for coupling said housing and said optical source;
said optical source is adapted to receive said modulated signal via said coupling means to provide a corresponding optical signal, and is adapted for underwater use; and
said holder is adapted to be positioned on the patient at a location which is remote from said housing.

22. A method for performing underwater monitoring on a patient, comprising the steps of:
- placing a transducer housing under water adjacent to a region of a patient to be monitored while the patient is giving birth under water;
- detecting a physiological function of the patient using the transducer;
- providing from the transducer an output signal indicative of the physiological function;
- modulating a carrier using the output signal;
- providing the output signal modulated carrier to an optical signal source;
- transmitting an optical signal from the optical signal source that corresponds to the output signal modulated carrier;
- receiving the optical signal; and
- recovering the output signal from the optical signal to monitor the physiological function.

23. The method of claim 22, further comprising the step of transmitting the optical signal in an infrared band.

24. The method of claim 22, further comprising the step of filtering out radiation interfering with the optical signal.

25. The method of claim 22, further comprising the step of detecting motion of the transducer housing.

26. The method of claim 25, further comprising the step of providing power to the transducer housing based on the transducer housing motion.

27. The method of claim 22 wherein the transducer housing comprises an ultrasound transducer.

28. The method of claim 22 wherein the waterproof transducer housing comprises a tocodynamometer transducer.

29. The method of claim 22 wherein the physiological function is fetal heart rate.

30. The method of claim 22 wherein the physiological function is uterine activity.

31. The method of claim 22 wherein the optical signal source is located under water such that the optical signal passes through a water-air boundary.

32. The method of claim 22 wherein the optical signal source is located above the water.

* * * * *